Figure 1:
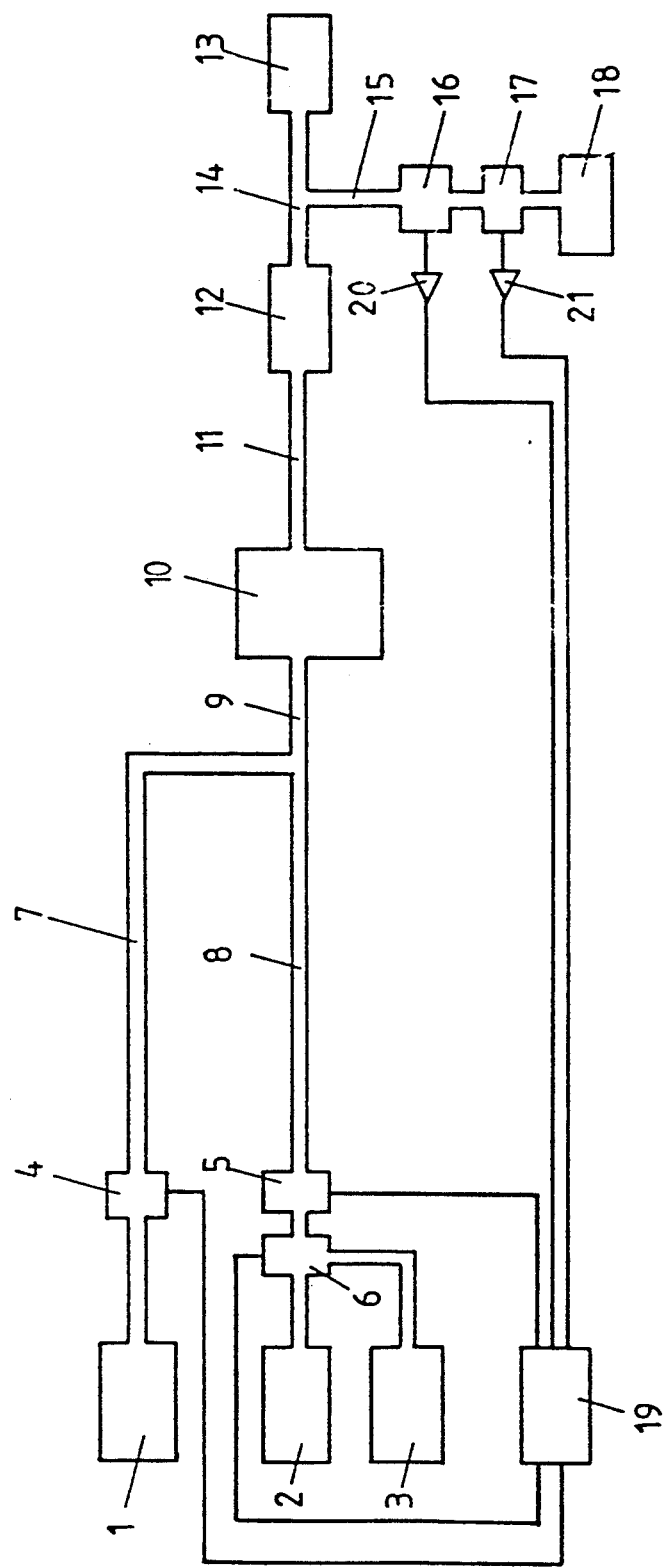

United States Patent [19]

Hakala

[11] Patent Number: 5,272,907
[45] Date of Patent: Dec. 28, 1993

[54] METHOD FOR THE IDENTIFICATION OF GASES

[75] Inventor: Matti A. Hakala, Helsinki, Finland

[73] Assignee: Instrumentarium Corporation, Finland

[21] Appl. No.: 711,758

[22] Filed: Jun. 7, 1991

[30] Foreign Application Priority Data

Jun. 8, 1990 [FI] Finland .................. 902895

[51] Int. Cl.⁵ .................................. G01N 33/00
[52] U.S. Cl. ..................... 73/23.2; 128/203.12; 128/204.21
[58] Field of Search ............... 73/23.2, 31.05; 128/204.21, 204.22, 205.11, 205.23, 203.12, 202.22

[56] References Cited

U.S. PATENT DOCUMENTS

| | | | |
|---|---|---|---|
| 3,817,085 | 6/1974 | Stubbs | 128/204.22 X |
| 3,927,977 | 12/1975 | Jacobs | 73/31.05 X |
| 4,150,670 | 4/1979 | Jewett et al. | 73/23.20 X |
| 4,215,409 | 7/1980 | Strowe | 128/204.22 X |
| 4,474,175 | 10/1984 | Hudimac, Jr. | 128/202.22 |
| 4,552,164 | 11/1985 | Urella | 128/204.22 X |
| 4,587,966 | 5/1986 | Albarda | 128/202.22 |
| 4,587,967 | 5/1986 | Chu et al. | 128/204.21 |
| 4,611,590 | 9/1986 | Ryschka et al. | 128/203.14 |
| 4,818,348 | 4/1989 | Stetter | 73/23.20 X |
| 4,832,014 | 5/1989 | Perkins | 128/203.12 |
| 4,903,693 | 2/1990 | Yasue | 128/203.12 |
| 4,907,441 | 3/1990 | Shurmer | 73/23.20 |
| 4,972,831 | 11/1990 | von dem Hagen et al. | 128/204.21 |
| 5,065,613 | 11/1991 | Lehnert et al. | 73/23.20 |

FOREIGN PATENT DOCUMENTS

| | | |
|---|---|---|
| 36285 | 9/1981 | European Pat. Off. . |
| 196157 | 10/1986 | European Pat. Off. . |
| 244794 | 6/1988 | European Pat. Off. . |
| 271109 | 6/1988 | European Pat. Off. . |
| 385256 | 9/1988 | European Pat. Off. . |
| 361134 | 4/1990 | European Pat. Off. . |
| 3706559 | 9/1988 | Fed. Rep. of Germany . |
| 3712598 | 10/1988 | Fed. Rep. of Germany . |
| 896328 | 9/1988 | Finland . |
| WO88/02890 | 4/1988 | PCT Int'l Appl. . |
| WO90/04164 | 4/1988 | PCT Int'l Appl. . |
| WO90/10212 | 9/1988 | PCT Int'l Appl. . |
| WO90/11507 | 10/1990 | PCT Int'l Appl. . |
| 8606638 | 11/1986 | World Int. Prop. O. ...... 128/204.22 |

Primary Examiner—Hezron E. Williams
Assistant Examiner—Joseph W. Roskos
Attorney, Agent, or Firm—Andrus, Sceales, Starke & Sawall

[57] ABSTRACT

The invention relates to a method for the identification of a gas, particularly an anaesthetic gas. The concentration measurement of a gas is carried out by two different methods, the application of at least one of the applied methods being infrared measuring, and said concentration measurements being followed by identification which is effected by utilizing both thus obtained measuring results and the corresponding values of prior known gases.

5 Claims, 1 Drawing Sheet

METHOD FOR THE IDENTIFICATION OF GASES

The present invention relates to a method for the identification of gases, particularly anaesthetic gases.

During anaesthesia, it is beneficial to measure the concentrations of gases respired by a patient. This is quite generally performed by using analyzer equipment based on the absorption of infrared radiation, capable of selectively measuring the concentrations of e.g. carbon dioxide and nitrous oxide or laughing gas.

Anaesthesia also involves the use of so-called volatile anaesthetics. The most common of these include halothane, enfluran and isofluran. As for their chemical structure, all these are halogenated organic compounds. They can also be measured by applying the above principle but, due to the similarity of their molecular structures, a problem is that the most useful absorption peak visible in infrared spectrum, originating from the oscillation of a C—H link at 3,3 um, is identical in all those compounds. Only the width and height of a C—H peak, and thus the sensitivity of measuring a particular substance, differ among each substance. Thus, the measuring method is not selective to a gas being measured—generally all organic gases and vapours absorb radiation on this wavelength.

In principle, it is also possible to develop an infrared absorption based apparatus, capable of identifying gases on the basis of their spectra. This can be carried out e.g. by studying the spectra of these substances on other wavelengths. This requires a transition to the wavelength range of 5-12 um, which causes problems in terms of components since normally employed infrared detectors do not function within this range, nor do the most common window materials transmit light on these wavelengths.

There is also another generally applied method for measuring the concentrations of said anaesthetics. This method is based on a crystal which is coated with a silicon-type substance. The coating material absorbs anaesthetics, the more absorption the higher the concentration thereof in a gas mixture being measured. Thus, the coating material mass will change so as to change also the resonance frequency of the crystal which can be measured by linking the crystal as part of an oscillator circuit. However, this method has exactly the same drawback as the infrared absorption method: it is not selective but sensitivity will depend on a substance being measured.

The most common measuring device for identifying anaesthetic gases is the mass spectrometer. Its most important drawback is its complicated structure and high price. Therefore, every hospital does not prossess such a device. However, if such an apparatus is available, it is generally in multiple use between several operating rooms and, thus, measured data is only obtained from a single patient at the intervals of several minutes. The recent developement has also produced relatively compact mass spectrometers which are intended for controlling or monitoring a single patient but they are still clearly more expensive than infrared equipment.

A relatively new measuring technique is Raman spectrometry. However, in terms of price and complicated structure it belongs in the same category as the above-mentioned single-patient mass spectrometers.

There are also prior known solutions, wherein a report of the anaesthetic being used is delivered manually to the apparatus by means of a keyboard. However, it is possible that the evaporator is filled with an incorrect substance or that the anaesthetic is to be replaced during the course of anaesthesia. This results in a hazard of a wrong gas being delivered to a patient, whereby the situation may even become dangerous to life.

An object of this invention is to overcome the above problems. Thus, the invention relates to a simple method for the identification of a gas, and particularly a gas used in anaesthesia, which method can be carried out by means of an apparatus having a low price.

The invention is based on the fact that the identification of gases is accompanied by measuring the gases by the application of two different methods. Such methods preferably include infrared absorption measuring and a method based on a change in the oscillating frequency of a crystal. For example, the sensitivity of an infrared analyzer to various anaesthetic gases is not identical in the same way as in an analyzer based on the change of a crystal oscillating frequency. However, the relative sensitivities of gases are totally different when applying these two methods. Thus, the identification of a gas is possible by combining these two measuring techniques and by utilizing such obtained measuring results and the corresponding data of prior known gases. The utilization is effected e.g. by calculating the ratio of measured signals and by comparing the obtained data to the comparative data of prior known gases acquired by a corresponding method.

The invention will now be described in more detail with reference made to the accompanying drawing, in which FIG. 1 shows a schematic view of a practical apparatus for carrying out the method of the invention.

Primarily, the figure shows a schematic view of an apparatus that can be used in the anaesthesia administration to a patient. The apparatus includes valves 4 and 5 serving as means for controlling gas flows from containers 1, 2 and 3. The fresh gas delivered to a patient consists e.g. of a mixture of either oxygen and nitrous oxide or alternatively of oxygen and air. The oxygen is contained in container 1 while container 2 holds the nitrous oxide and container 3 holds the air. A valve 6 is operated to select either one of the gases of containers 2 or 3.

Conduits 7 and 8 leading from the containers join each other and this combined flow of gases is carried along a conduit 9 to a vapourizer 10, wherein the gas flow is mixed with an anaesthetic. Thence, the flow will continue along a conduit 11 through a ventilation unit 12 to a patient 13. To a conduit 14 leading from the ventilation unit to a patient is attached another conduit 15 which extends to analyzers 16 and 17. A pump 18 is used to aspirate a sample from tube 14 to the analyzers. The analyzers preferably comprise an infrared analyzer and an analyzer detecting a change in the crystal oscillating frequency. Signals received from the analyzers are carried to a processor 19 by way of preamplifiers 20 and 21.

In anaesthesia, the functions of processor 19 preferably include a possibility of adjusting a desired oxygen/laughing gas ratio or oxygen/air ratio and a desired total gas flow by means of valves 4, 5 and 6.

The identification of a gas is effected by performing two different measurements, which are preferably the above-mentioned infrared absorption measurement and the measurement based on a change in the crystal oscillating frequency and by using e.g. processor 19 to calculate the ratio of signals received therefrom preferably as follows: The signal issued by an infrared analyzer is $S_1$ and the signal from an analyzer based on a change in the crystal oscillating frequency is $S_2$, respectively. These signals are supposedly linearized so as to be directly proportional to the concentration of a substance being measured in a gas mixture. It is prior known that the following equations apply to various gas types:

$$S_1 = k_{a1} c$$

$$S_2 = k_{a2} c,$$

wherein ka1 and ka2 are constants characteristic of a given substance and c is the concentration of a substance being measured in a gas mixture. With all anaesthetics, a fact is that $$k_{a1} \neq k_{a2}.$$

It is also known that, with all anaesthetics, the ratio $$S_1/S_2 = k_{a1}/k_{a2}$$

is different and characteristic of a given substance. Thus, an anaesthetic being measured can always be identified by calculating said ratio and by comparing it to prior known ratios characteristic of various substances. A quantitative determination of concentration can be effected on the basis of either signal after the identification of a gas.

Since the above two measurements are impossible to fit physically together, there will be in practice some phase shift between the signals and this complicates the calculation of a proper signal ratio on the basis of momentary values. Therefore, in view of a gas identification it is preferable to determine the maximum values e.g. for both signals over a single respiration cycle or, for still improved accuracy, to determine an average over several respiration cycles as well as to calculate a ratio thereof. A delay induced by the calculation of an average is not critical in view of identification.

When studying anaesthetic gases, the infrared measuring is preferably effected at 3,3 um with the oscillation of a C—H link being detectable.

The actual infrared absorption measurement and the measurement based on a change in the crystal oscillating frequency are not described in detail in this Patent application, since both methods are familiar to artisans and descriptions of the operation thereof can be found in the literature. However, these methods have never been together for the identification of gases.

The drawing only illustrates one possible identification method but a variety of other possibilities exist within the scope of the annexed claims. The invention, which is directed to an identification method of gases, is by no means limited to its application in anaesthesia alone but it is highly applicable in other contexts as well.

It is obvious that signals received with two different measuring methods need not necessarily be divided among themselves followed by comparing the obtained ratio to corresponding prior known values but, instead, these recorded values of prior known gases can be either multiplied or divided with either one of the measuring values received from a gas being studied and this result can be compared to the other measuring result which has not yet been utilized.

What is claimed is:

1. A method for the qualitative identification of a gas found in a gaseous volume, said method comprising the steps of:

measuring the infrared absorption characteristic of said gas and generating an absorption value corresponding thereto;

estimating the concentration of said gas based upon said absorption value, and generating a first measurement signal corresponding to said estimated concentration;

measuring the change of the oscillating frequency of a crystal which is exposed to said gas and generating a change value corresponding thereto;

estimating the concentration of said gas based upon said change value and generating a second measurement signal corresponding to said estimated concentration; and employing said first measurement signal, said second measurement signal and a data characteristic of a known gas to identify the gas.

2. The method of claim 1, wherein said employing step further comprises:

obtaining a ratio of said first and second measurement signals; and comparing said ratio with a data ratio of a known gas to identify the gas.

3. The method of claim 1, wherein said employing step further comprises:

multiplying a value functionally related to said first measurement signal with a value functionally related to said data characteristic of said known gas to yield a result; and comparing the result of said multiplication with a value functionally related to said second measurement signal to identify said gas.

4. The method of claim 1, wherein said employing step further comprises:

multiplying a value functionally related to said second measurement signal with a value functionally related to said data characteristic of said known gas to yield a result; and comparing the result of said multiplication with a value functionally related to said first measurement signal to identify said gas.

5. The method of claim 1, wherein said gas is an anaesthetic gas.

* * * * *